United States Patent
Letzt et al.

(10) Patent No.: US 7,664,657 B1
(45) Date of Patent: Feb. 16, 2010

(54) HEALTHCARE COMMUNICATIONS AND DOCUMENTATION SYSTEM

(75) Inventors: Alan Letzt, Purcellville, VA (US); Jacob P. Lefkowtz, Springfield, VA (US); Dianne F. Kaseman, Boyd's, MD (US)

(73) Assignee: Vocollect Healthcare Systems, Inc., Pittsburgh, PA (US)

( * ) Notice: Subject to any disclaimer, the term of this patent is extended or adjusted under 35 U.S.C. 154(b) by 357 days.

(21) Appl. No.: 10/997,625

(22) Filed: Nov. 24, 2004
(Under 37 CFR 1.47)

Related U.S. Application Data (60) Provisional application No. 60/525,017, filed on Nov. 25, 2003.

(51) Int. Cl.
G06Q 10/00 (2006.01)
G06Q 50/00 (2006.01)

(52) U.S. Cl. .......................................... 705/2
(58) Field of Classification Search .................. 705/2
See application file for complete search history.

(56) References Cited

U.S. PATENT DOCUMENTS

| | | | |
|---|---|---|---|
| 5,077,666 A | | 12/1991 | Brimm et al. |
| 5,536,084 A | | 7/1996 | Curtis et al. |
| 5,822,544 A | * | 10/1998 | Chaco et al. .................... 705/2 |
| 5,838,223 A | * | 11/1998 | Gallant et al. ............ 340/286.07 |
| 5,986,568 A | * | 11/1999 | Suzuki et al. ............ 340/825.52 |
| 6,292,783 B1 | | 9/2001 | Rohler et al. |
| 6,591,242 B1 | * | 7/2003 | Karp et al. ..................... 705/2 |
| 6,714,913 B2 | | 3/2004 | Brandt et al. |
| 6,720,864 B1 | * | 4/2004 | Wong et al. ................. 340/7.52 |
| 6,747,556 B2 | * | 6/2004 | Medema et al. ........ 340/539.12 |
| 7,065,381 B2 | | 6/2006 | Jenkins et al. |
| 7,283,845 B2 | * | 10/2007 | De Bast ........................ 455/566 |
| 7,287,031 B1 | * | 10/2007 | Karpf et al. .................. 707/100 |

* cited by examiner

*Primary Examiner*—C. Luke Gilligan
*Assistant Examiner*—Reginald Reyes
(74) *Attorney, Agent, or Firm*—Wood, Herron & Evans, LLP

(57) ABSTRACT

A communications and documentation system is disclosed that improves staff communication, education, and/or documentation. This system is interactive and integrates speech recognition, telephony, wireless, and/or database technologies, and innovative algorithms in a novel way that allows for assigning staff, scheduling staff activities, and data collection and reporting. The system also incorporates features that promote ease of use by persons who are not skilled at using technology.

29 Claims, 4 Drawing Sheets

HEALTHCARE COMMUNICATIONS AND DOCUMENTATION SYSTEM

This application claims the benefit of U.S. Provisional Application(s) No.: 60/525,017 Filed Nov. 25, 2003

TECHNICAL FIELD OF THE INVENTION

The present invention relates to an interactive voice activated communications, information, and/or documentation system. The present invention can be used, for example, in a healthcare facility such as a nursing home (a) by nurses or other healthcare professionals to assign, manage, and monitor staff and patients via real-time computer reports, and (b) by nursing assistants or other staff to receive their remaining assignments and other information, to document patient care, and to communicate with other staff. The present invention can also be used to provide other functions such as education, reporting, reminders, scheduling, and management functions.

BACKGROUND OF THE INVENTION

In a nursing home, a supervisory nurse or other healthcare professional is responsible for managing the work of several nursing assistants, assessing patient needs, and providing additional patient care. Nursing assistants are responsible for conducting or assisting with patients' "activities of daily living", which include but are not limited to bathing, dressing, grooming, meals, and transfers. All work must be documented for regulatory and legal reasons.

Documenting patient care is a time consuming task that is traditionally performed with pen and paper and that takes away from time spent with patients. Moreover, such "manual documentation" is often illegible. Staff learns their care plans by reading paper-based plans that are constantly being updated or by talking to the nurse. They do not always have the most up-to-date information.

Recently, wall mounted computers and personal digital assistants (PDAs) have been used by staff in some facilities to enter patient data. Such systems are extremely challenging and stressful for nursing assistants, who typically fear technology or may otherwise find such technology difficult to use.

Also, PDAs have small keys that are difficult to use and small screens that are difficult to read. Wall mounted computers cannot be located at an ergonomically correct height for all staff, and compliance with legislation (e.g., Health Insurance Portability and Privacy Act) that protects patient privacy is problematic. Further, touch screen versions of wall mounted computers promote bacteria transmission by the staff who use them. Bedside computers offer a more costly alternative and do not resolve the problems with training staff on computer use and the spread of infections.

Staff also needs to communicate with each other to discuss observations or to request assistance with patient care. The present alternatives, such as searching the corridors and rooms, yelling down the hall, or using a traditional speaker based paging system, are time consuming, noisy, and disruptive, and intercom systems used at some facilities require the staff to be physically near the intercom terminals when help is needed.

In addition, staff requires constant training to keep up with new methods and healthcare advances. This training is traditionally accomplished in person and occasionally with audio and video tapes and other presentation equipment. As a result, current training methods require the staff to be in a location where they are unable to provide patient care.

Moreover, nurses communicate with physicians and family members of their patients in person and by phone while referring to paper based charts. It is often time consuming to find the charts, which may be in use by others. In addition, information from paper based charts that is entered into a computer system is typically several days out of date.

Therefore, it would be desirable for the long-term care industry and other care providing environments to have a lightweight, mobile, voice-activated, hands-free technology for improved documentation, communication, information dissemination, and education. It would also be desirable for this technology to operate in real time so that the staff is always working with up-to-date information, and the information is readily available in some form to all authorized persons.

The present invention presents a novel way of overcoming one or more of these or other problems.

SUMMARY OF THE INVENTION

In accordance with one aspect of the present invention, a method of providing care to patients implemented by wireless transmission between at least one mobile terminal and a server comprises the following: audibly receiving a user voice message by the mobile terminal, wherein the user voice message is spoken by a user of the mobile terminal; wirelessly transmitting the user voice message from the mobile terminal to the server; matching the user voice message to a corresponding response voice message associatively stored by the server; wirelessly transmitting the response voice message from the server to the mobile terminal; wirelessly receiving the response voice message at the mobile terminal; and, audibly reproducing the response voice message for hearing by the user.

In accordance with another aspect of the present invention, a method performed by a personal terminal is provided to receive instructions regarding the care of a patient by a care provider and to transmit information relating to the care provided to the patient by the care provider. The personal terminal is located remotely from a database, and the database stores the instructions provided to the care provider and the information provided by the care provider. The method comprises the following: receiving the instructions, wherein the instructions identify the patient and the care to be provided to the patient; audibly reproducing the instructions for hearing by the care provider; receiving the information from the care provider by way of spoken messages; and, wirelessly transmitting the information to the database.

In accordance with yet another aspect of the present invention, a server for a care provider communication and documentation system comprises a speech recognition engine, a database, and a speech output device. The speech recognition engine receives and interprets a spoken message from a remote terminal, and the spoken message relates to care given to persons. The database stores response messages regarding care to be given to the persons. The speech output device communicates one of the response messages back to the remote terminal when the one response message corresponds to the spoken message.

In accordance with still another aspect of the present invention, a care provider communication and documentation system comprises at least one remote terminal, a speech recognition engine, a database, and a speech output device. The at least one remote terminal is used by a care provider to receive first voice messages containing instructions related to the care of a patient and to transmit second voice messages containing information related to the care provided to the patient by the care provider. The speech recognition engine receives and interprets the second voice messages from the at least one remote terminal. The database stores the first voice messages. The speech output device communicates one of the first voice messages back to the remote terminal when a corresponding one of the second voice messages is recognized by the speech recognition engine as matching the one of the first voice messages.

In accordance with a further aspect of the present invention, a method of providing care to a patient implemented by at least one terminal used by a care giver to give care to the patient comprises the following: audibly receiving a user voice message by the terminal, wherein the user voice message is spoken by the care giver and relates to the care of the patient; transmitting the user voice message from the terminal to a server; receiving a response voice message at the terminal, wherein the response message is automatically generated at the server, and wherein the response voice message relates to care of the patient; and, audibly reproducing the response voice message for hearing by the care giver.

In accordance with yet a further aspect of the present invention, a method of transmitting messages comprises the following: receiving an information request; if the requested information relates to a scheduled activity, transmitting a scheduled message (S) related to the scheduled activity; if the requested information relates to a scheduled activity and a scheduled message (S) related to the scheduled activity is transmitted, transmitting a tied message (T), if any, that is tied to the transmitted scheduled message (S); and, if there is an information message (I) to transmit, transmitting the information message (I) whether or not the scheduled message (S) is transmitted and whether or not the tied message (T) is transmitted.

BRIEF DESCRIPTION OF THE DRAWINGS

These and other features and advantages will become more apparent from a detailed consideration of the invention when taken in conjunction with the drawings in which.

DETAILED DESCRIPTION

Figure 1:
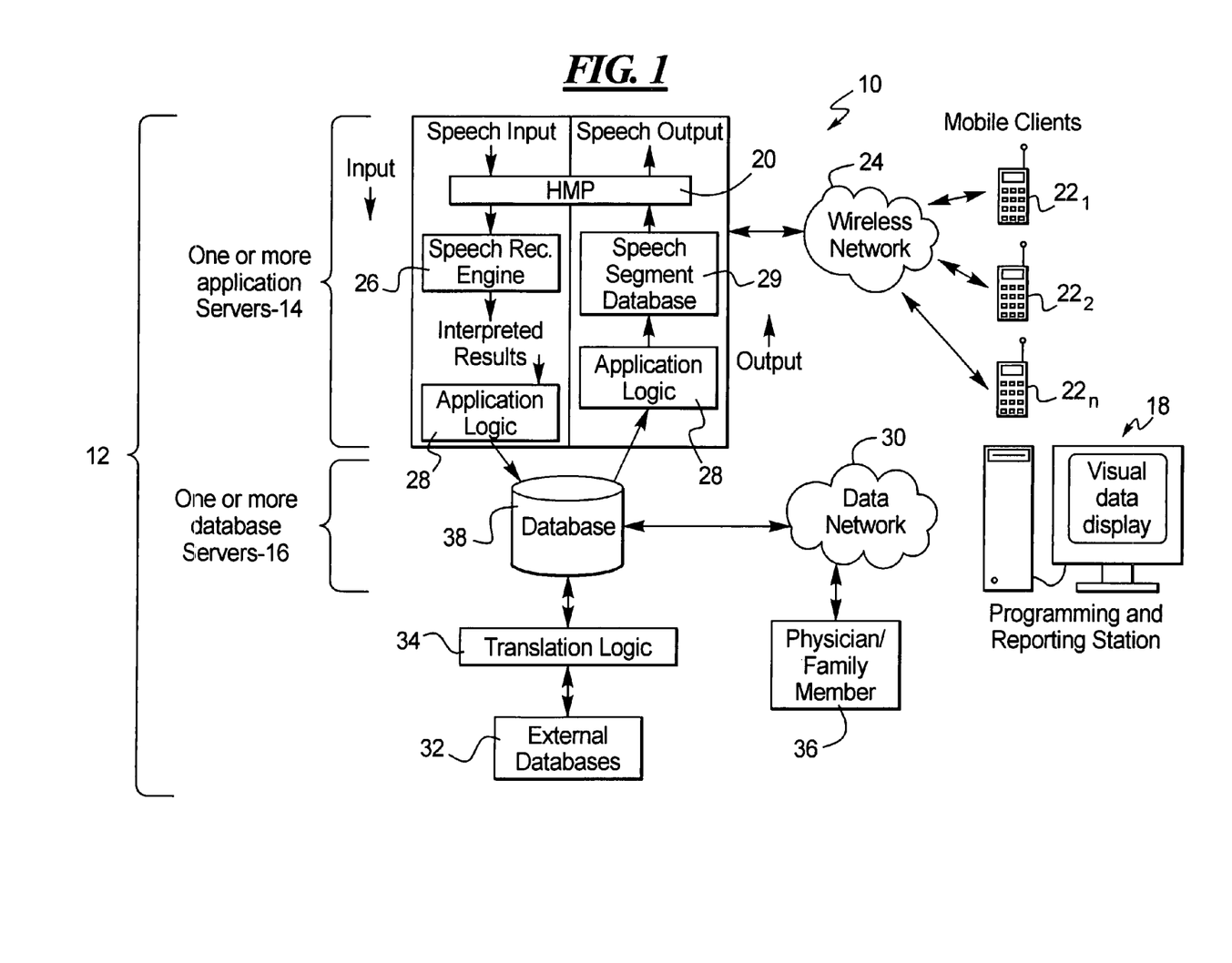
FIG. 1 illustrates a healthcare communication and documentation system in accordance with an embodiment of the present invention.

As shown in FIG. 1, a communication and documentation system 10 useful in providing care to persons includes a server 12 containing an application portion 14 and a database portion 16. The server 12, for example, may comprise one or more computers. For example, the application portion 14 can reside on one or more computers or servers, and the database portion 16 can reside on one or more computers or servers. The server 12 provides both database and web server capabilities.

A host computer 18, which may be a standard desktop personal computer, provides an interface which can be used, for example, by a supervisor or nurse (a) to enter and update patient care plans and associated data, (b) to enter patient care requirements that are linked to speech segments that can be retrieved when needed by staff members at any time, (c) to enter staff member assignments such as which patients are assigned to which staff members on a given shift, (d) to schedule patient tasks that result in the server 12 calling the staff members at scheduled times (e.g., to communicate appointment reminders), and (e) to enter other information that is linked to the server 12. This other information can include, for example, the names of new staff members and/or new patients. This information is then integrated by the server 12 into dialogues (e.g., James Jones gets dressing; or Hello Mary Smith).

The host computer 18 can also be used (a) to generate reports based on patient data (e.g., vital signs, falls) entered either by voice or by use of a screen display on the host computer 18, (b) to display text in a screen display (e.g., that indicates that a NOTE is available for a patient and that includes a LINK that can be clicked on in order to listen to the NOTE through a headset where the NOTE is archived in the form of a sound file, and (c) to generate reports on staff performance (e.g., productivity reports indicating the number of tasks recorded per hour and exception reports that indicate activities not completed by staff members for each resident.

Moreover, the host computer can further be used to set system parameters, to conduct training sessions, to provide immediate advice on the care of patients, and to perform additional or alternative functions.

The host computer 18, for example, may include a standard web browser in order to support communications between the host computer 18 and the server 12. However, alternative apparatus may be used to support communications between the host computer 18 and the server 12.

The server 12 contains host media processing software 20. This software, for example, is obtainable from Intel Corporation and can support bi-directional voice communication with the users of mobile terminals $22_1, 22_2, \ldots, 22_n$.

The database portion 16 of the server 12 supports database connectivity for the communication and documentation system 10. The database portion 16 provides a central repository for all communication and documentation system data and, thus, acts as a bridge between the mobile terminals $22_1, 22_2, \ldots, 22_n$ and the host computer 18.

The mobile terminals $22_1, 22_2, \ldots, 22_n$ can be any type of suitable devices such as cordless telephones, portable data assistants (PDAs), Notebook PCs, Tablet PCs, and/or other mobile devices equipped to wirelessly communicate with the server 12. A computerized device that is not mobile, such as a landline telephone, may also be used to communicate with the server 12 in the same manner as a mobile user device. In one embodiment of the present invention, the mobile terminals $22_1, 22_2, \ldots, 22_n$ can be SpectraLink NetLink cordless telephones that operate using 802.11b wireless Voice-Over-Internet-Protocol, and thus communicate directly with telephony hardware of the server 12. The H.323 protocol may be used for call control.

Also, the mobile terminals $22_1, 22_2, \ldots, 22_n$ may be arranged to communicate with the server 12 and with each other using any desired network such as a wireless Internet Protocol network 24.

Accordingly, examples of communications in the communication and documentation system 10 comprise the following: (i) Voice-Over-Internet-Protocol (VoIP) calls; (ii) calls that retrieve selected sound files stored on the server 12 and that play the sound files to the staff members over the mobile terminals $22_1, 22_2, \ldots, 22_n$; (iii) interactive calls that interpret the staff members' key presses on the mobile terminals $22_1, 22_2, \ldots, 22_n$; (iv) interactive calls that process the staff members' speech by sending it to a speech recognition engine 26 in the application portion 14 for interpretation and for storing of the interpretation results as text files on an application logic 28 of the database portion 16; and, (v) interactive calls that process the staff members' speech by recording it as a file stored on the application logic 28.

As described above, the mobile terminals $22_1, 22_2, \ldots, 22_n$ are located on the same wireless Internet Protocol network 24 as the server 12. Appropriate routes can be established in the wireless Internet Protocol network 24 by software settings so that calls are directed to the server 12. The server 12 uses the speech recognition engine 26, which executes speech recognition software, such as from ScanSoft, Inc., to interpret spoken responses from the users of the mobile terminals $22_1, 22_2, \ldots, 22_n$ and to convert them into text that can be processed by application logic 28 of the telephony system.

Based on the interpretation results, the server 12 executes software in the application logic 28 that matches the text equivalent of the voice message (for example, requesting a patient's bathing schedule) received from the user of the mobile terminal 22 to corresponding text stored in the database portion 16 in order to select the appropriate responses from the database portion 16. For example, the text equivalent of the voice messages can be used as pointers into the database portion 16 to retrieve the appropriate responses. Alternatively, the voice messages can be used a pointers into the database portion 16 without first converting the voice messages to text. The application logic 28 assembles speech segments selected from a speech segment database 29 based on the responses into complete voice messages. These complete voice messages are then transmitted as voice signals to the mobile terminal 22 using the host media processing software 20.

The server 12 and the mobile terminals $22_1, 22_2, \ldots, 22_n$ may be located, for example, in the same local area as the staff members that use them. In an alternative embodiment, the server 12 and the mobile terminals $22_1, 22_2, \ldots, 22_n$ may be connected to the public Internet and the server 12 can be located at a different site from the mobile terminals $22_1, 22_2, \ldots, 22_n$.

The host computer 18 and the server 12 communicate through a data network 30. The supervisor enters, updates, or corrects patient care information data using a mouse or other data entry device. Furthermore, data may be exported to and imported from an external database 32 by way of translation logic 34 included in the software of the communication and documentation system 10.

The supervisor can use the host computer 18 to review data collected via the communication and documentation system 10 on patient care and staff member performance in the form of real time host interface reports. For this purpose, the host computer 18 includes a report generator that generates reports based on data stored in the database portion 16. In addition, selected reports from the host interface provided by the host computer 18 can be made available to physicians and family members on their computers 36 through a secure web site or web connection.

The application software of the communication and documentation system 10 is comprised of dialogue scripts that control the "conversation" between the staff members and the server 12. These scripts can follow rules that establish how messages in the communication and documentation system 10 are linked to each other in a database 38 of the database portion 16. Sample scripts are shown in Appendix A.

Accordingly, the database 38 of the communication and documentation system 10 includes a speech file database that stores a set of prerecorded responses, the text of all of the elements of patient care information, the patient data entered by the users of the mobile terminals $22_1, 22_2, \ldots, 22_n$ and the host computer 18, and the voice messages recorded by the users via the mobile terminals $22_1, 22_2, \ldots, 22_n$. Based on the responses stored in the database 38, the application logic concatenates the speech segments stored in the speech segment database 29 to assemble all possible voice responses of the communication and documentation system 10 to staff member commands.

The software of the communication and documentation system 10 converts the patient care messages selected on the host computer 18 to speech messages and establishes relationships between the patient care activities. The selected patient care messages are then made available to be heard on the mobile terminals $22_1, 22_2, \ldots, 22_n$ at scheduled times or time intervals or otherwise.

Every message is characterized as either (i) a scheduled message (S), (ii) a message (T) that is tied into, and to be played in conjunction with, a scheduled message (S), or (iii) an information message (I) that is for information only and does not, therefore, require a specific activity to be completed.

"S-messages" can be heard by the staff members over the mobile terminals $22_1, 22_2, \ldots, 22_n$ any time during the prescribed time interval. The prescribed time interval, for example, may be the time of a staff member's shift or some other time interval entered by use of the host interface of the host computer 18. "S-messages" stay active during the prescribed time interval until the staff member reports the activity as completed, at which point they are removed from the list of active messages and are reported as completed in the database portion 16 of the communication and documentation system 10. When the activity is reported to be completed, the "S-messages" are also removed from the list of uncompleted activities displayed by the host interface provided by the host computer 18.

"T-messages" are active during the same time period as the associated "S-messages".

"I-messages" are active and available for the user to hear at all times.

All patient care activities tracked by the communication and documentation system 10 may be scheduled at specific times of the day for each patient. This scheduling allows the staff member to hear only relevant activities over the mobile terminals $22_1, 22_2, \ldots, 22_n$ in the order in which they need to be completed for the current shift time period. For example, the Day Shift staff will hear that they must complete Breakfast and Lunch, in that order. They will not hear that they must complete Dinner, because that occurs on the Evening Shift.

The staff members can enter patient data by speaking a number such as temperature. The software of the communication and documentation system 10 establishes an acceptable range for each parameter and each entry must be within this range to be accepted. If the entry is not within the acceptable range, the communication and documentation system 10 asks the staff member to try again.

The communication and documentation system 10 provides scheduled outbound calls with messages for the users (staff members) of the mobile terminals $22_1, 22_2, \ldots, 22_n$ at specific times based on scheduling provided through use of the host interface provided by the host computer 18. Each scheduled call may be simultaneously directed to specified one(s) of the mobile terminals $22_1, 22_2, \ldots, 22_n$ without a user request. The user(s) of the specified one(s) of the mobile terminals $22_1, 22_2, \ldots, 22_n$ may either accept the call or ask the communication and documentation system 10 to call back later.

The communication and documentation system 10 can also provide unscheduled outbound calls when a staff member says a specified word option into the mobile terminal 22. For example, saying "Emergency" will result in all logged in staff members receiving an emergency call. Other such outbound calls can be triggered by a staff member's voice command or by a set of specified system conditions.

In one embodiment of the invention, each staff member wears a headset that is connected to the corresponding mobile terminal 22. This headset enables the staff member to "converse" hands free with the communication and documentation system 10 from any place within the area covered area by the wireless system antennas and at any time. Thus, the staff members can obtain their latest assignments, ask for patient care information, hear patient care messages, input patient data, record the completion of a patient care activity, talk directly to other staff members wearing headsets and logged into the communication and documentation system 10, and/or record spoken messages that can be accessed by other staff member on the same shift or later shifts.

Figure 2:
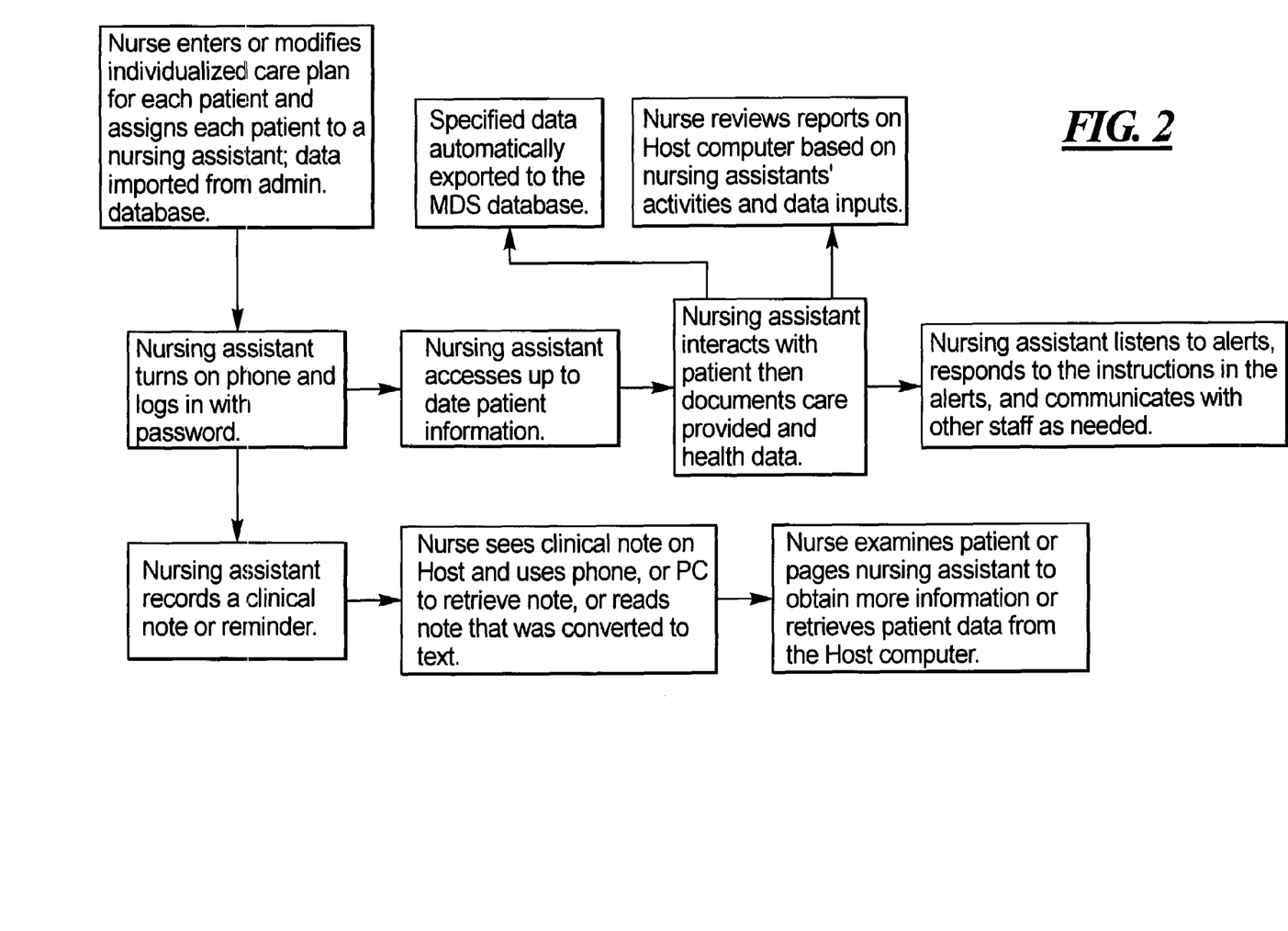
FIG. 2 is a flow chart illustrating the use of the healthcare communication and documentation system of FIG. 1.

A schematic that provides an example of the overall process is shown in FIG. 2. The flexible design of the communication and documentation system 10 is not strictly hierarchical and, thus, the sequence of events can vary to meet the user's needs.

As shown by the process of FIG. 2, the supervisor, using the host computer 18, enters or modifies the individualized care plan for each patient and assigns each patient to a staff member. This data is imported to the server 12 from an administrative database stored, for example, on the host computer 18. The staff member turns on his or her mobile terminal 22 and logs in with the appropriate password. Thereafter, the process of FIG. 2 follows one of two paths.

Along one of these two paths, the staff member speaks into the corresponding mobile terminal 22 to record a clinical note or to record a reminder to send a message to the server 12. The supervisor using the host computer 18 sees a message on the host computer interface that a clinical note is available for retrieval and listens to the note through a voice interface or reads the note that has been converted to text and displayed on the host computer interface.

Along the other path, the staff member uses one of the mobile terminals $22_1$, $22_2$, ..., $22_n$ to access assignments and/or up-to-date patient care information of interest. The staff member then documents the care provided to, and the health data of, the patient using one of the mobile terminals $22_1$, $22_2$, ..., $22_n$. The care and health data are automatically exported to the database portion 16 for storage as described herein. Also, the supervisor reviews such stored care and health data on the host computer 18. Moreover, the staff members use the mobile terminals $22_1$, $22_2$, ..., $22_n$ to communicate with other staff members as needed.

The users must log in to start using and to be recognized by the communication and documentation system 10 and must log out when finished using the system. The dialogues of the communication and documentation system 10 are designed for primarily non-hierarchical navigation, allowing the user to rapidly move from one dialogue section to another when hearing a response message. In an alternative embodiment, a hierarchical dialogue structure may be used. Appendix A illustrates typical dialogues in a nursing home environment, consistent with FIG. 2.

The following list includes additional features that can be incorporated into the communication and documentation system 10: triggering a call to a supervisor and posting an alert note on the host interface provided by the host computer 18 when patient data, such as blood pressure, is out of a pre-defined "clinically acceptable range"; allowing a user to enter and correct data using either one of the mobile terminals $22_1$, $22_2$, ..., $22_n$ or the host interface of the host computer 18, and retaining an audit trail of changes; recognizing unavailability of staff (e.g., staff on lunch break) to receive an outbound call and redirecting such call to another person logged into the system; reading data inputs from written or printed data sheets that are scanned and storing such data in the database portion 16; automatically inactivating a message for a specified time period when a patient is designated to not receive such message for such specified time period; notifying staff members when a patient is designated to not receive a message for a specified time period; reading data from a bar code or radio frequency identification (RFID) scanner or other scanning device and storing such data in the database portion 16; allowing a free-form spoken message to be recorded, converted to text by commercially available speech-to-text software, displayed by the host interface, and stored in the database portion 16 as a text message; scheduling reminder messages to the mobile terminals in advance of the reminded activity, where the amount of advance notice may vary by message type; sending an alert message to a mobile terminal that a change in patient care has been entered on the host interface; sending an alert message to a mobile terminal when a parameter in a patient's record has changed; automatically reviewing and analyzing patterns of data in the database portion 16 and sending an alert message to a mobile terminal when the data analysis indicates that a critical value or range was exceeded; sending a reminder or educational message to the mobile terminal when a patient is to receive a specified type of care by the user; sending a reminder or educational message to the mobile terminal when specified types of data are entered by the user; sending a reminder to the mobile terminal about the patient's personal information, such as a birthday; sending an outbound message to all mobile terminals simultaneously; causing the mobile terminals $22_1$, $22_2$, ..., $22_n$ to automatically log out at the end of a shift after notification of the users; causing the host interface provided by the host computer 18 to automatically log out at the end of a shift after notifying the users; interfacing the communication and documentation system 10 to third party wireless systems such as nurse call systems via interface software such as that provided by SpectraLink and converting the alerts produced by the wireless system into a text or speech message on the mobile terminal; interfacing the communication and documentation system 10 with a telephone system so the mobile terminals $22_1$, $22_2$, ..., $22_n$ can make calls via a public telephone network; interfacing the communication and documentation system 10 with third party software in a way that allows review of data on the host interface before the data are exported to the third party software; capturing a telephone message from an authorized caller from outside the facility and recording such message as a voice or text note in the database portion 16; and, a word option on the mobile terminal that retrieves previously recorded data such as vital signs and that communicates such data to the user in a voice message.

Figure 3:
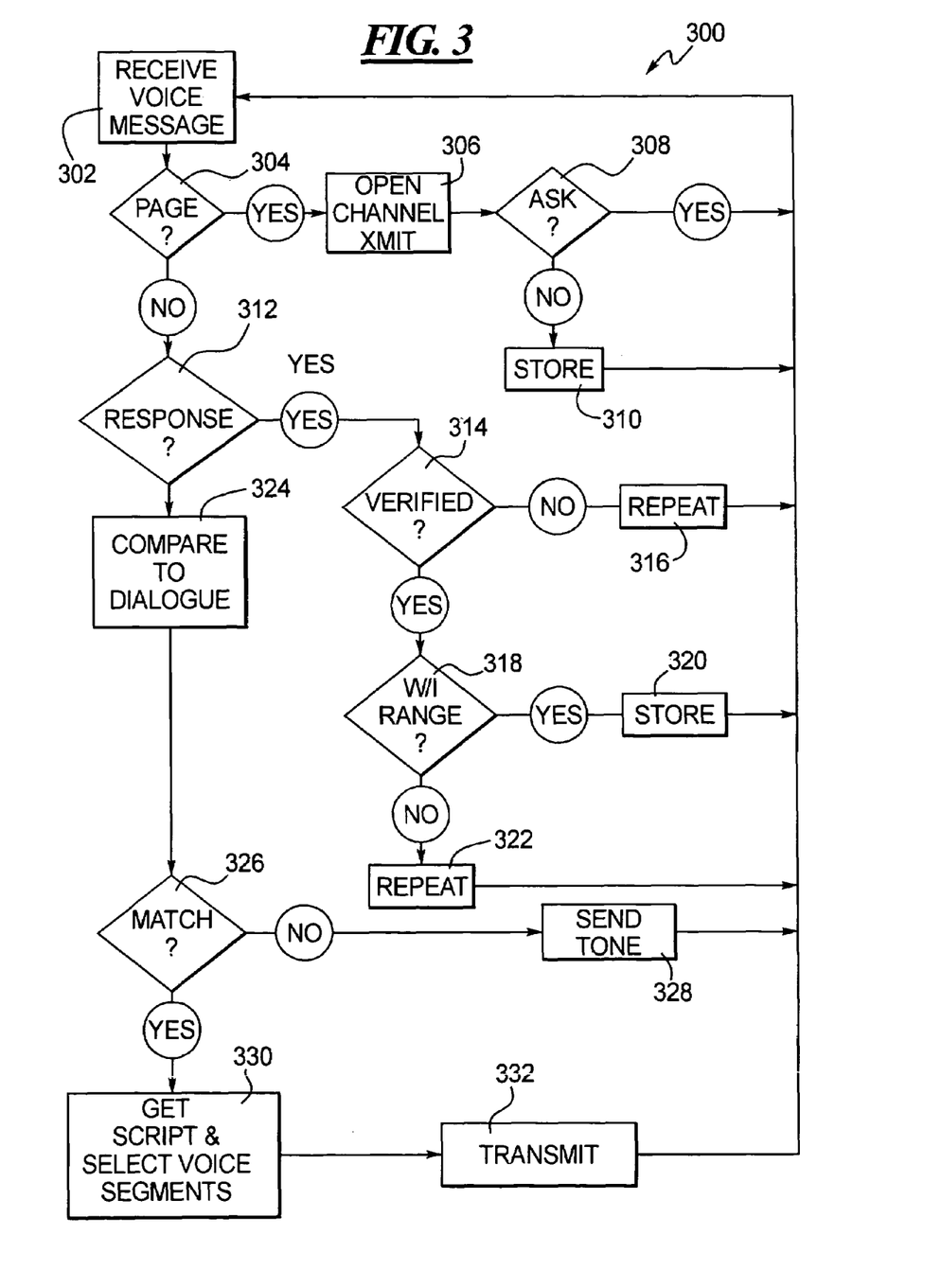
FIG. 3 is a flow chart representing a program that may be executed by the healthcare communication and documentation system of FIG. 1; and, FIG. 4 is a flow chart representing another program that may be executed by the healthcare communication and documentation system of FIG. 1.

The application logic 28 executes a program 300 to perform the functions as described herein. FIG. 3 is a high level flow chart which illustrates the program 300 of the application logic 28. When a voice message is received by the server 12 from one of the mobile terminals 22 as indicated by a block 302, a check is made at a block 304 to determine whether the message is a page in which a staff member using the mobile terminal 22 is paging an individual staff member or is paging a group of other staff members.

If the received message is a page, a channel is opened and the page is transmitted at a block 306. If the individual being paged acknowledges the page as determined at a block 308, the individual staff member and the page originator use the mobile terminals as telephones to conduct a conversation, and program flow returns to the block 302. If a group of staff members being paged acknowledge the page as determined at a block 308, the staff members in the group hear a message recorded by the group page originator by speaking into the mobile terminal when the group page is placed, and program flow returns to the block 302. However, if all staff members being paged do not acknowledge the page, the identities of those staff members not acknowledging the page are stored at a block 310 so that those staff members can be paged at a later time, the staff members acknowledging the page hears a message recorded by the originator of the group page by speaking into the mobile device when the group page is placed, and program flow returns to the block 302.

If the received message is not a page, a determination is made at a block 312 as to whether the received message is information, such as a response to a question previously asked by the server 12 of the user of the mobile terminal 22, or a word option that engages the server in a continued dialogue. If the message is a response containing information to be stored, a determination is made at a block 314 as to whether the user has verified the information (this verification step may be skipped in some cases as with many YES/NO responses). If the information has not been verified, then a request is made of the user at a block 316 to verify the information and program flow returns to the block 302. If the received information is verified, a determination is made at a block 318 as to whether the information has a range check associated with it and whether the information is within the valid range. If so, the information is stored at a block 320, a next message in the dialogue, if any, is transmitted to the mobile terminal, and program flow returns to the block 302. If the received information is not in the valid range, or if the received information is not verified, the server 12 transmits a request for retransmission of the information at a block 322 and program flow returns to the block 302.

If the received message is not information, the received message is compared to the dialogue stored in the database portion 16. A determination is then made at a block 326 to determine if the received message matches any of the dialogue stored in the database portion 16. If not, the received message must contain an invalid word option and the system cannot act on the received information and thus communicates its inability to proceed to the staff member with a tone or message at a block 328. Program flow then returns to the block 302.

If the received message matches the dialogue stored in the database portion 16, the matching response stored in the database portion 16 is retrieved from the database portion 16 at a block 330 and is transmitted at a block 332. Program flow then returns to the block 302.

Figure 4:
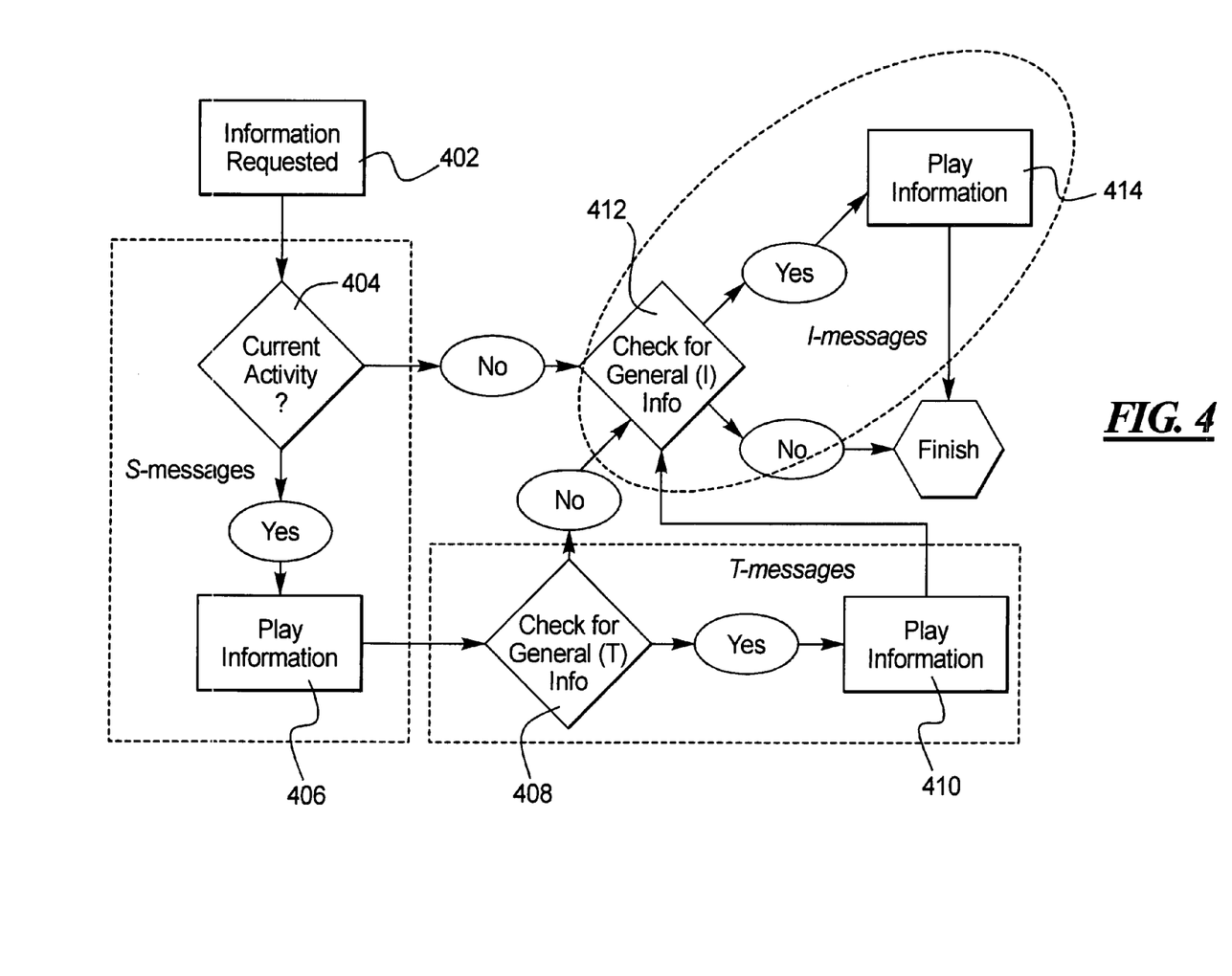

FIG. 4 is a flow chart of a program that can be executed by the block 330 when a request for information is received by the server 12. Specifically, when the part of the dialogue initiated by the staff member through use of a mobile terminal 22 is a request for information as indicated at a block 402, a check is made at a block 404 to determine if the information requested relates to a current activity, i.e., whether the request relates to an activity to occur during a scheduled time period, for example the current shift.

The blocks 402 and 404 can be arranged to cover different types of scheduled activities. For example, some scheduled messages may occur only once during the scheduled time period such that, if the activity has already been performed, the message is not played. Some scheduled messages may occur a fixed number of times greater than one during the scheduled time period such that, if the activity has been performed less than the prescribed number of times, the scheduled message is played. Some scheduled messages may have a start and stop time and must be performed every X hours such that, if current time is between the specified start and stop times, the scheduled message is played along with a message stating the timeframe and stating that the last time activity was performed, regardless of how many times it has been performed.

If the requested information relates to a current activity, the requested information is played at a block 406. That is, the requested information is assembled from speech segments into a complete voice message and the voice message is transmitted at the block 332. This message is referred to above as a scheduled message (S).

Thereafter, a check is made at a block 408 to determine if there is a tied message (T) tied into, and to be played in conjunction with, the scheduled message (S). If there is a tied message (T) tied into the scheduled message (S), the tied message is played at a block 410.

If the requested information does not relate to a current activity as determined at the block 404, or if there is no tied message (T) tied into the scheduled message (S) as determined at the block 408, of after the tied message is played at the block 410, a check is made at a block 412 to determine if there is an information message (I) to be played. If there is an information message (I) to be played, the information message (I) is played at a block 414. After the information message (I) is played at the block 414, or if there is no information message (I) to be played as determined at the block 412, the routine of FIG. 4 is ended and program flow returns to the block 302 of FIG. 3.

The communication and documentation system 10 can be used in a variety of care giving settings including nursing homes, assisted living facilities, hospitals, home healthcare facilities, and rehabilitation centers.

Therefore, the terms "supervisor" and "staff member" as used herein are meant to be generic to cover any person capable of using the communication and documentation system 10 for its intended purpose. Similarly, the term "patient" as used herein is meant to be generic to cover other people, such as assisted care and/or nursing home residents, who receive care by the users of the communication and documentation system 10.

APPENDIX A. SAMPLE DIALOGUES

LOGIN Process—At the beginning of the shift, each user (staff member and/or supervisor) logs in to the communication and documentation system 10. The login process allows the communication and documentation system 10 to link the user with the user's patient assignments. Here is an example with a fictitious healthcare professional using the communication and documentation system 10. The material not in brackets represent verbal dialogue.

LOGIN PROCESS - Passcode is correct
Definitions: SM: Staff Member
CDS: Communication and Documentation System

| | |
|---|---|
| SM: | [Press the specified button on the mobile terminal] |

-continued

| | LOGIN PROCESS - Passcode is correct<br>Definitions: SM: Staff Member<br>CDS: Communication and Documentation System |
|---|---|
| CDS: | Please log in |
| SM: | [Keys in correct passcode on mobile terminal] |
| CDS: | Donald Smith. Is this correct? |
| SM: | YES. |
| CDS: | <Ending tone> |

The ending tone signals to the user that the communication and documentation system 10 is finished speaking and it is now the user's turn.

ASSIGNMENT Option—The ASSIGNMENT option allows the staff member to review his or her patient assignment list.

| | ASSIGNMENT OPTION (Beginning of shift) |
|---|---|
| SM: | ASSIGNMENT |
| CDS: | You have activities assigned for 5 patients. Miranda Miller Room 290; Chris Culbertson Room 291; James Jackson Room 292; Betty Erving Room 293; and Penny Henderson Room 311A. |
| CDS: | <Double beep> |

RESIDENT OPTION—The RESIDENT option allows the staff member to access a care plan and database associated with a specific patient to either hear or record information about such patient. In the option, the staff member speaks the resident's room number, and the communication and documentation system 10 then allows the staff member to get or record patient related information.

For example, the communication and documentation system 10 can retrieve many types of information that is sent to the mobile terminal as voice messages including: (i) BACKGROUND when spoken elicits background information that is individualized to the patient, (ii) TASK LIST when spoken elicits information that includes activities of daily living in the care plan during a particular shift, (iii) <A SPECIFIC TASK NAME> when spoken elicits messages with details for a specific task (e.g., the task name GROOMING when spoken may elicit a message at the mobile terminal such as "provide wig care", and (iv) <A SPECIFIC DATA NAME> when spoken elicits a message with the most recently recorded data for the patient (e.g., the data name WEIGHT when spoken may elicit a message at the mobile terminal such as "the patient's weight is 150 pounds"). Following are some examples:

| SM: | TASK LIST |
|---|---|
| CDS: | James Jackson Room 292 needs vital signs, bathing, mouth care, dressing, grooming, meals, toilet, positioning, transfers, and ambulation. |
| CDS: | <Ending tone> |
| SM: | GROOMING. |
| CDS: | James Jackson Room 292. Caution: He is diabetic. Check with nurse before grooming. He needs a shave. Use an electric razor. |

-continued

| CDS: | <Ending tone> |
|---|---|
| SM: | TEMPERATURE. |
| CDS: | James Jackson Room 292. The temperature on September 2nd at 3:15 PM was 99.8 degrees Fahrenheit. |
| CDS: | <Ending tone> |

Similarly, after a staff member has spoken a patient's room, the staff member can tell information to the communication and documentation system 10 information about a patient at the point of care. This information will be automatically recorded in the patient's database. The kinds of patient information that the nursing assistant can tell include: (i) <SPECIFIC TASK NAME> DONE when spoken allows the staff member to document the completion of a specific task (e.g., the words "Grooming Done" when spoken may elicit at the mobile terminal a question such as "Has the patient had breakfast?"; and, (ii) <SPECIFIC DATA NAME> when spoken allows the staff member to speak patient data to be recorded into the mobile terminal (e.g., the word option "PULSE" when spoken may elicit in the mobile terminal a question such as "What is the pulse?"). Following are some examples:

| SM: | PULSE |
|---|---|
| CDS: | What is the pulse? |
| SM: | 86. |
| CDS: | 86. Is this correct? |
| SM: | YES. |
| CDS: | <Ending tone> |
| SM: | MEALS DONE |
| CDS: | James Jackson, room 292. |
| SM: | YES. |
| CDS: | Did the patient eat lunch? |
| SM: | YES. |
| CDS: | What was the percentage of meal eaten? |
| SM: | 75. |
| CDS: | 75 percent. Is this correct? |
| SM: | YES. |
| CDS: | What was the fluid intake in ccs? |
| SM: | 100. |
| CDS: | 100 ccs. Is this correct? |
| SM: | YES. |
| CDS: | How many calories? |
| SM: | 500. |
| CDS: | 500 calories. Is this correct? |
| SM: | YES. |
| CDS: | <Ending tone> |

Other options can also be provided using similar dialogues. For example, NOTE when spoken allows the nurse to record a note or to listen to one or more previously recorded notes. NOTE in the RESIDENT allows the staff member to record a note or to listen to a note about a specific patient. After recording, the staff member may be offered the options of saving, adding to, deleting and listen to the note. A skip option can also be used to allow the user to skip to the next note by saying the option word SKIP.

PAGE when spoken enables a user to talk with one or more other staff members as discussed above.

REPORT when spoken enables the staff member to hear the end-of-shift report from the previous shift at any time.

Certain modifications of the present invention have been described above. Other modifications of the present invention will occur to those practicing in the art of the present invention. For example, although as described above staff members are the users of the mobile terminals 22, the supervisor of the staff members can also use a mobile terminal to communication with the server 12 and/or with the staff members.

Accordingly, the description of the present invention is to be construed as illustrative only and is for the purpose of teaching those skilled in the art the best mode of carrying out the invention. The details may be varied substantially without departing from the spirit of the invention, and the exclusive use of all modifications which are within the scope of the appended claims is reserved.

We claim:

1. A method of caring for a plurality of patients, the method comprising:
    maintaining, in a database, instructions regarding individualized care plans of a plurality of patients;
    capturing a spoken message from a care provider at a personal terminal remote from the database;
    using a speech recognition program to process the captured spoken message to determine the content of the spoken message;
    accessing patient care instructions in response to the content of the spoken message, wherein the instructions are associated with at least one patient and with the individualized care plan of the at least one patient for directing care that is to be provided to the patient;
    audibly reproducing the instructions as part of a speech dialogue for being heard by the care provider;
    receiving information from the care provider, relating to the care that is provided to the patient for the individualized care plan, by way of additional spoken messages and the use of the speech recognition program; and,
    wirelessly transmitting the information to the database.

2. The method of claim 1 wherein the personal terminal comprises: a telephone.

3. The method of claim 2 wherein the telephone comprises a wireless telephone.

4. The method of claim 1 wherein the personal terminal comprises a wireless mobile terminal.

5. The method of claim 1 wherein the information wirelessly transmitted by the mobile terminal is related to vital signs of the patient.

6. The method of claim 1 wherein the information wirelessly transmitted by the mobile terminal is related to grooming of the patient.

7. The method of claim 1 wherein the information wirelessly transmitted by the mobile terminal is related to feeding of the patient.

8. The method of claim 1 further comprising transmitting a page to another care provider.

9. The method of claim 1 further comprising transmitting information that includes an indication that care has been given.

10. The method of claim 1 further comprising transmitting key presses from the personal terminal.

11. The method of claim 1 further comprising initiating a call from the personal terminal to another personal terminal.

12. The method of claim 1 further comprising receiving an ending tone indicating that a dialogue is completed.

13. The method of claim 1 wherein the patient care instructions include automatically generated patient care instructions that identify the patient and the care to be provided to the patient.

14. The method of claim 1 further comprising:
    the spoken message including an information request from the care provider;
    if the requested information relates to a scheduled activity, transmitting a scheduled message (S) related to the scheduled activity;
    if the requested information relates to a scheduled activity and a scheduled message (S) related to the scheduled activity is transmitted, transmitting a tied message (T), if any, that is tied to the transmitted scheduled messaged (S); and
    if there is an information message (i) to transmit, transmitting the information message (I) whether or not the scheduled message (S) is transmitted and whether or not the tied message (T) is transmitted.

15. The method of claim 14 wherein the information request is wirelessly captured, and wherein the scheduled message (S), the tied message (T), and/or the information message (I) are wirelessly transmitted.

16. The method of claim 14 wherein the information request, the scheduled message (S), the tied message (T), and the information message (I) are part of an audible dialogue.

17. The method of claim 14 wherein the transmitting of a scheduled message (S) comprises transmitting of the scheduled message (S) if the requested information relates to a scheduled activity, if currently within a time range specified for the scheduled activity, and if the scheduled activity has not been completed.

18. The method of claim 1 wherein the spoken message includes a request for patient assignments from the care provider, and wherein the patient care instructions include the patient assignments for the care provider.

19. The method of claim 1 wherein the spoken message includes a request for tasks for an assigned patient, and wherein the patient care instructions include tasks to be performed for the assigned patient.

20. The method of claim 1 wherein the spoken message includes the initiation of a recording of a note.

21. A method of caring for a plurality of patients comprising:
    maintaining patient care information for at least one patient as an individualized care plan for the at least one patient;
    at a terminal associated with a care provider, capturing speech from the care provider;
    using a speech recognition program to process the captured speech to determine the content of the spoken message;
    accessing patient care information from the individualized care plan associated with the at least one patient in response to the content of the spoken message;
    audibly playing the patient care information of the individualized care plan to be heard by the care provider;
    capturing, at the terminal, further speech from the care provider relating to the care that is provided to the at least one patient by the care provider and using the speech recognition program on the captured further speech to generate patient care data;
    maintaining that patient care data in a database.

22. The method of claim 21 wherein the patient care information is related to vital signs of the patient.

23. The method of claim 21 wherein the patient care information is related to personal care of the patient.

24. The method of claim 21 wherein the patient care information is related to feeding of the patient.

25. The method of claim 21 wherein the patient care Information is related to toileting for the patient.

26. The method of claim 21 wherein the patient data includes an indication that patient care has been completed.

27. The method of claim 21 wherein the captured speech includes a request for patient assignments, the accessed patient care information including patient assignments for the care provider.

28. The method of claim 21 wherein the captured speech includes a request for tasks for a patient, the accessed patient care information including tasks to be performed for a patient by the care provider.

29. The method of claim 21 wherein the captured speech includes a request for data for a patient, the accessed patient care information including data associated with a patient.

* * * * *

UNITED STATES PATENT AND TRADEMARK OFFICE
CERTIFICATE OF CORRECTION

| | | |
|---|---|---|
| PATENT NO. | : 7,664,657 B1 | Page 1 of 1 |
| APPLICATION NO. | : 10/997625 | |
| DATED | : February 16, 2010 | |
| INVENTOR(S) | : Alan Letzt et al. | |

It is certified that error appears in the above-identified patent and that said Letters Patent is hereby corrected as shown below:

Column 5, line 25 reads "...can be used a pointers..." and should read -- ...can be used as pointers... --.

Column 13, lines 32-33, CLAIM 2 reads "...the personal terminal comprises: a telephone." and should read -- the personal terminal comprises a telephone. --.

Column 14, lines 4-5, CLAIM 14 reads "...is tied to the transmitted scheduled messaged..." and should read -- ...is tied to the transmitted scheduled message... --.

Signed and Sealed this
Fifth Day of March, 2013

Teresa Stanek Rea
*Acting Director of the United States Patent and Trademark Office*